United States Patent [19]

Tezuka

[11] Patent Number: 4,861,411
[45] Date of Patent: Aug. 29, 1989

[54] METHOD OF PRODUCING GEL SHEET FOR ELECTROPHORESIS

[75] Inventor: Shigeru Tezuka, Saitama, Japan

[73] Assignee: Fuji Photo Film Co., Ltd., Kanagawa, Japan

[21] Appl. No.: 246,408

[22] Filed: Sep. 19, 1988

[30] Foreign Application Priority Data

Jan. 20, 1988 [JP] Japan ................................. 63-10453

[51] Int. Cl.$^4$ .................. B29C 39/00; B32B 31/18
[52] U.S. Cl. .............................. 156/344; 156/584;
156/268; 156/242; 156/246; 156/247; 156/500;
156/501; 156/510; 156/267; 264/212;
204/180.1; 204/182.8; 204/299 R
[58] Field of Search ............ 204/182.8, 249 R, 180.1;
83/151, 100, 102, 107, 152, 154; 156/344, 584,
268, 267, 242, 246, 247, 500, 501, 510; 264/212

[56] References Cited

U.S. PATENT DOCUMENTS 4,699,680 10/1987 Shiraishi et al. ............... 204/299 R

FOREIGN PATENT DOCUMENTS 5337979 4/1978 Japan ..................................... 83/152

*Primary Examiner*—John F. Niebling
*Assistant Examiner*—John S. Starsiak, Jr.
*Attorney, Agent, or Firm*—Jules E. Goldberg

[57] ABSTRACT

In a method of producing a gel sheet for electrophoresis comprising a gel membrane acting as the medium for electrophoresis composed of a hydrophilic polymer having a uniform thickness, two sheets of transparent or translucent electrical insulating films disposed on the front and the rear surfaces of the gel membrane and two pieces of spacers disposed along two facing sides of the gel membrane, an end not provided with the spacer of the gel membrane is cut off to form a slot for loading samples, the improvement which comprises, punching the gel membrane, before one surface of the gel membrane is covered with said electrical insulating film yet, to form the portion corresponding to the slot for loading samples, pressing an adhering member on the cut piece of gel membrane thereby sticking at least an edge of the cut gel membrane piece thereon, and removing the adhering member holding the cut piece of gel membrane therefrom.

In the method of the invention, the cut gel membrane piece can be removed easily, surely and completely. As a result, the processing speed is raised to about four times compared to the conventional method.

5 Claims, 5 Drawing Sheets

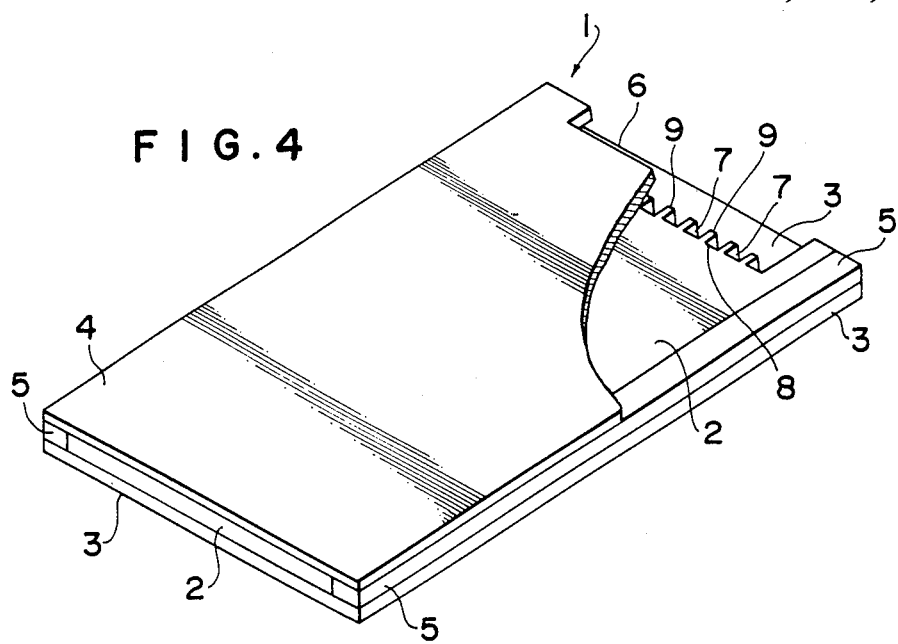
F I G. 4
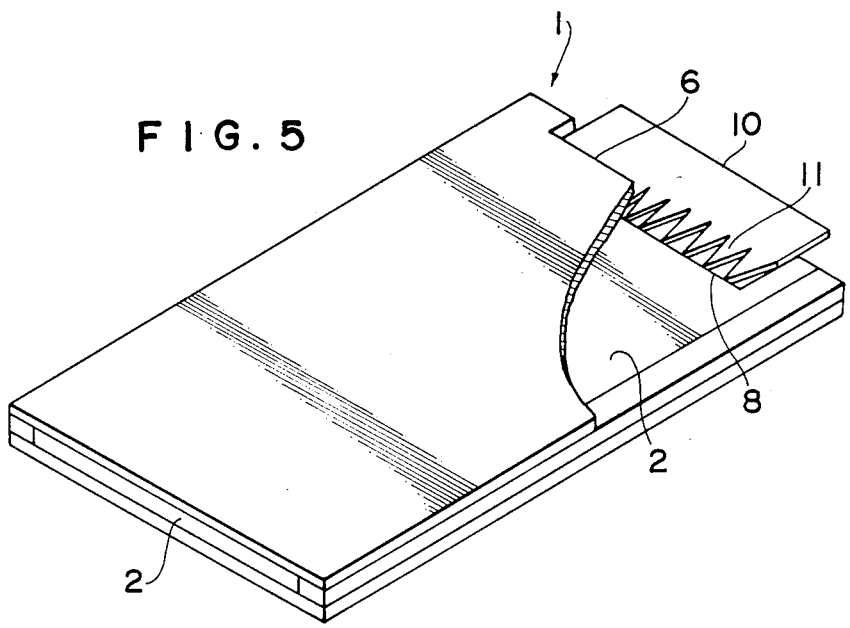
F I G. 5

METHOD OF PRODUCING GEL SHEET FOR ELECTROPHORESIS

BACKGROUND OF THE INVENTION

1. Field of the Invention

This invention relates to a method of producing a gel sheet for electrophoresis. More particularly, this invention relates to a method of providing a slot for loading samples into the gel sheet for electrophoresis.

2. Description of the Prior Art

An electrophoresis widely utilized is used for separating or analyzing high-molecular materials capable of having a charge in a solution such as proteins, nucleic acids and their decomposition products in a sheet medium, suc as gel membrane or filter paper, containing a buffer solution based upon the difference of charge and molecular weight.

Particularly, in gene engineering field, an important technique is the determination of base sequence of an isotope-labeled nucleic acid by utilizing autoradiography. In the electrophoretic operation for this purpose, a base-specific reaction product (mixture) of an isotope-labeled DNA or DNA fragment is allowed to migrate in parallel in electric field. Electrophoresis of a series of base-specific reaction products are, in general, carried out in one electrophoretic sheet, and plural electrophoretic patterns are formed in parallel. The electrophoretic migration patterns obtained as autoradiograms are compared with each other, and the base sequence is determined.

For conducting electrophoresis using gel membrane consisting of starch, polyacrylamide or the like as the electrophoretic medium, heretofoe, the person to conduct electrophoresis has to prepare each time a gel membrane on a flat plate such as glass plate. Such preparation work was troublesome, and it was a great load for the person to conduct electrophoresis.

Recently, a sheet material for electrophoresis called gel sheet (Japanese Patent KOKAI 126237/1984) has been commercially available. The gel sheet 1, as shown in Figure 4, is composed of the gel membrane 2 for electrophoresis, a base film 3 and a cover film 4 disposed on the front and the rear of the gel membrane 2 respectively, and a pair of spacers 5, 5 disposed along both sides of the gel membrane 2. The base film 3 and the cover film 4 of non-rigid electrical insulating material such as polyester film, are usually in contact with the gel membrane 2. An end of the gel membrane 2 is indented across most of the width so as to form a slot 6 for loading samples between the base film 3 and the cover film 4. A series of rectangular wells 7, 7, . . . ,7 for placing sample solutions are closely formed at the bottom 8 of the slot 6. The upper edge of the cover film 4 is slightly cut off so that a sample solution is easily put into the well 7. End projection 9 partitioning the slot 6 into respective wells 7 has a width of more than 1 mm, therefore, a space of a similar width is formed between respective electrophoretic migration regions called lanes. In case that the comparison of respective electrophoretic migration patterns is necessary, such as in the case of DNA base sequence analysis where the comparison is carried out as to a series of fragments having four kinds of bases (A, G, C, T), such space should be omitted or as small as possible. Therefore, a method of using a plate member having a sawtooth-shaped portion has been developed for such requirement, as shown in FIG. 5. The member 10 is called shark's teeth comb, and inverse V-shaped projections 11, 11, . . . 11 are formed at regular intervals in the teeth portion. In this method, the bottom 8 of the slot 6 is made straight, and the shark's teeth comb 10 is inserted into the slot 6, till respective tips of the inverse V-shaped projections 11 come into contact with or partly inserted into the upper edge of the gel membrane 2. Then, sample solutions are injected into each triangular or trapezoidal well formed by the projections of the shark's teeth comb 10 and the bottom 8 of the slot 6.

The above gel sheet 1 for electrophoresis is assembled, for example, by the process of FIG. 3 disclosed in Japanese Patent KOKAI No. 203847/1985, using either the gel sheet of FIG. 4 or the gel sheet of FIG. 5. In this process, a web of the base film 3 is delivered from its wound roll, and spacers 5, 5 delivered from their rolls are stuck to both side portions of the web of the base film 3. A gel-forming liquid composition is poured in film-shape from a hopper 12 on the web of the base film 3 so as to fill the whole space formed by the upper face of the web and two spacers 5, 5 with the liquid. Then, the gel-forming liquid composition is cured by passing it through a curing chamber 13 to form the gel membrane 2 for electrophoresis. The gel membrane 2 is punched by a punching means 14, and the cut piece of gel membrane is removed to form the portion corresponding to the "upper" (meaning that it is attached the upper end of upright type electrophoresis apparatus) edge of the gel membrane 2 in thegel sheet 1. A web of the cover film 4 is delivered from its wound roll, and stuck on the web of the gel membrane 2 supported by the base film 3. Then, the web is cut by the cutter 15 at each prescribed position to complete the gel sheet 1. In the above process of prior art, the punching process is carried out, as shown in FIG. 6. In the drawing, a half-assembled web moves intermittently in the leftward direction, and at each stop time, the pressure-controled chamber 17 of the punching means 16 descends. The gel membrane 2 is punched by a punching blade (not illustrated) provided on the underside of the pressure-controled chamber 17, and the cut piece of gel membrane 18 is adsorbed by the suction through the suction pipe 19. The pressure-controled chamber 17 holding the cut piece 18 ascends, and the receiving pan 20 comes under the pressure-controled chamber 17. After the suction pipe 19 is closed, the air supply pipe 21 connected to the pressure-controled chamber 17 is opened. While, the suction pipe 22 connected to the receiving pan 20 is opened, then the cut piece 18 is adsorbed to the receiving pan 20. The receiving pan 20 returns to the original place, and the cut piece 18 can be discharged by pressurizing through an air supply pipe 23. Thus, the procedure of one cycle is completed, and the next cycle is repeated.

In the above method, however, the suction was not effected uniformly depending on the position in the cut piece 18, and a fragment of the cut piece often remained on the gel sheet 1 as shown in the part X of FIG. 6. Moreover, a part of the cut piece 18 was stuck to the pressure control chamber 17, and could not be transferred to the receiving pan 20, as shown in the part Y of FIG. 6.

When such a state once happened, the working efficiency was remarkably lowered, since the fragment should be removed from the gel membrane 2 or the pressure control chamber 17 by hand.

SUMMARY OF THE INVENTION

An object of the invention is to provide a method of producing a gel sheet for electrophoresis having a slot for loading samples efficiently wherein a fragment of the cut gel membrane piece does not remain on the punched gel membrane nor on the punching means.

Another object of the invention is to provide a method of producing a gel sheet for electrophoresis having a slot for loading samples, particularly using a shark's teeth comb, efficiently wherein a fragment of the cut gel membrane piece does not remain on the punched gel membrane nor on the punching means.

The present invention provides a method which has been achieved the above objects, and it is characterized by that, in a method of producing a gel sheet for electrophoresis comprising a gel membrane acting as the medium for electrophoresis composed of a hydrophilic polymer having a uniform thickness, two sheets of transparent or translucent electrical insulating films disposed on the front and the rear of the gel membrane and two pieces of spacers disposed along both sides of the gel membrane, an end not provided with the spacer of the gel membrane is cut off to form a slot for loading samples, the improvement which comprises, punching the gel membrane, before one face is covered with the above electrical insulating film yet, to form the portion corresponding to the slot for loading samples, pressing an adhering member on the cut piece of gel membrane thereby sticking at least an edge of the cut piece of gel membrane thereon, and removing the adhering member holding the cut piece of gel membrane therefrom.

BRIEF DESCRIPTION OF THE DRAWINGS

FIG. 4 is a partially cutaway perspective view of a gel sheet for electrophoresis.

FIG. 5 is a partially cutaway perspective view of another gel sheet for electrophoresis using a shark's teeth comb.

DETAILED DESCRIPTION OF THE INVENTION

The gel sheet to be produced by the method of the invention is known. For example, Japanese Patent KOKAI Nos. 126237/1984, 296255/1986 and Japanese Patent Application No. 190999/1986 disclose useful gel sheets having a polyacrylamide gel membrane as the medium for electrophoresis. The medium may be an agarose gel membrane, a starch membrane or the like.

The production method of the gel sheet may be the same as a known method, such as disclosed in Japanese Patent KOKAI No. 203847/1985, except the punching and removing process for forming the slot for loading samples. That is, a gel-forming liquid composition composed of polyacrylamide or the like is poured and spreaded over the face of the base film with spacers stuck along at both side edges thereof, and cured to form a gel membrane on the base film. The gel membrane is punched, and the cut piece is removed to form the portion corresponding the slot for loading samples by the method explained hereafter. A part of the base film neighboring to the slot portion is punched, and then, the cover film is stuck on the gel membrane.

The gel membrane may be punched according to a known method, such as disclosed in Japanes Patent KOKAI No. 220852/1987 and the methods disclosed therein as the prior art.

The punched shape is not limited, and usually a rectangle.

The adhering member comprises a material capable of adhering to the gel membrane and separating it from the parts of the gel sheet adhering thereto. The adhering member preferably has a hydrophilic surface, and includes filter paper, nonwoven fabric and the thermoplastic resin films, such as composed of cellulose acetate or polyethylene terephthalate, of which the surface is rendered hydrophilic by physical or chemical treatment. As the surface treatment, there are the incorporation of a surfactant, glow discharge, corona discharge, gelatin coating, a hydrophilic synthetic polymer coating, colloidal silica coating, saponification and the like. They are well known as the treating method of the support used for photographic photosensitive materials.

The shape of the adhering member may be any shape capable of adhering to the gel membrane separating it from the base film of the gel sheet, and may be tape, roller, plate or the like. A tape member is preferable.

The adhering member is allowed to adhere to at least an edge of the cut gel membrane piece by pressing the member toward the membrane. The edge may be in a longitudinal direction or a lateral direction. Adhering the member to almost whole surface of the cut gel membrane piece is the most preferable.

The moving direction and the passage of the adhering member is set so as to stick the cut gel membrane piece and to separate it from the base film of the gel sheet.

In the method of the invention, the cut gel membrane piece can be removed easily, surely and completely. As a result, the processing speed is raised to about four times compared to the conventional method.

EXAMPLE

Figure 1:
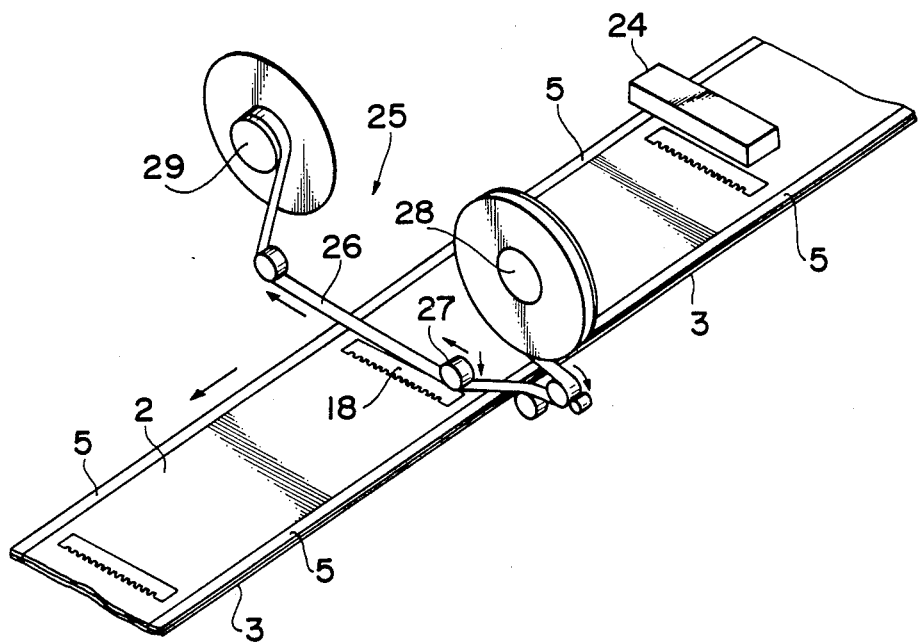
FIG. 1 is a perspective view of a punching means and a removing means used for the method of the invention.
Figure 2:
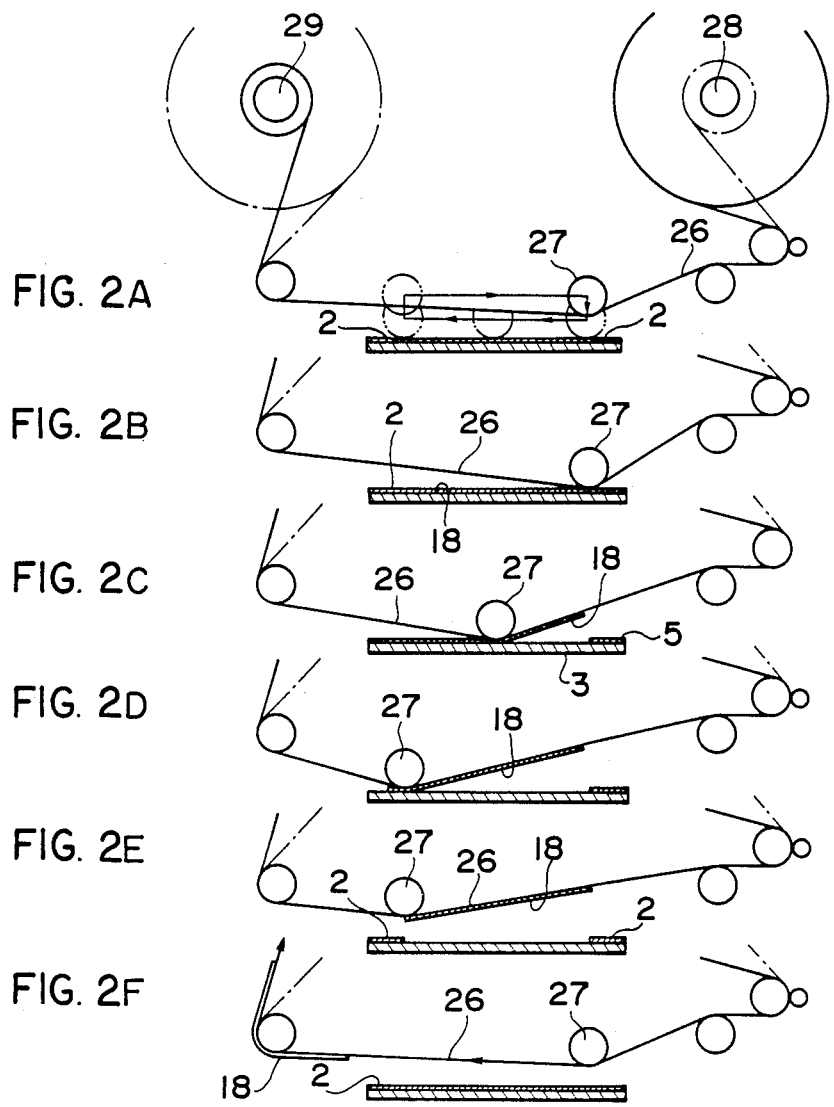
FIG. 2 is a side view indicating a series of actions to separate and remove the cut gel membrane piece from a punched web of the gel membrane.

An example of the method of the invention is explained making reference to FIGS. 1 and 2. The punching and removing means used for this example is composed of a puncher 24 and a remover 25 disposed at the position 14 in FIG. 3.

The puncher 24 is movable in a vertical direction, and a punching blade (not illustrated) not sticking the gel membrane is provided on the underside.

The remover 25 is disposed behind the puncher 24 close thereto, and composed of an adhering tape 26 made of filter paper ("Advantec Toyo Tape No. 131", Toyo Roshi Kaisha Ltd.) and a pressure roller 27. The tape 26 is coiled around a delivery roll 28, and delivered through several rolls in the cross direction to the web to a take-up roll 29. The pressure roller 27 is provided upward the web in contact with the upside of the adhering tape 26, and is movable in a vertical direction and the cross direction to the web.

Figure 3:
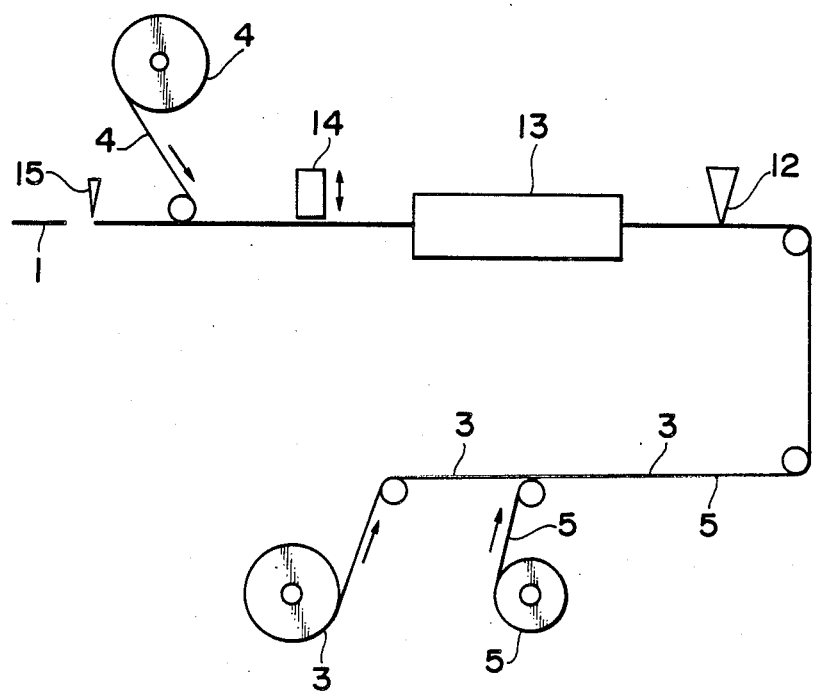
FIG. 3 is a schematic flow diagram indicating a process of the invention for producing a gel sheet.
Figure 6:
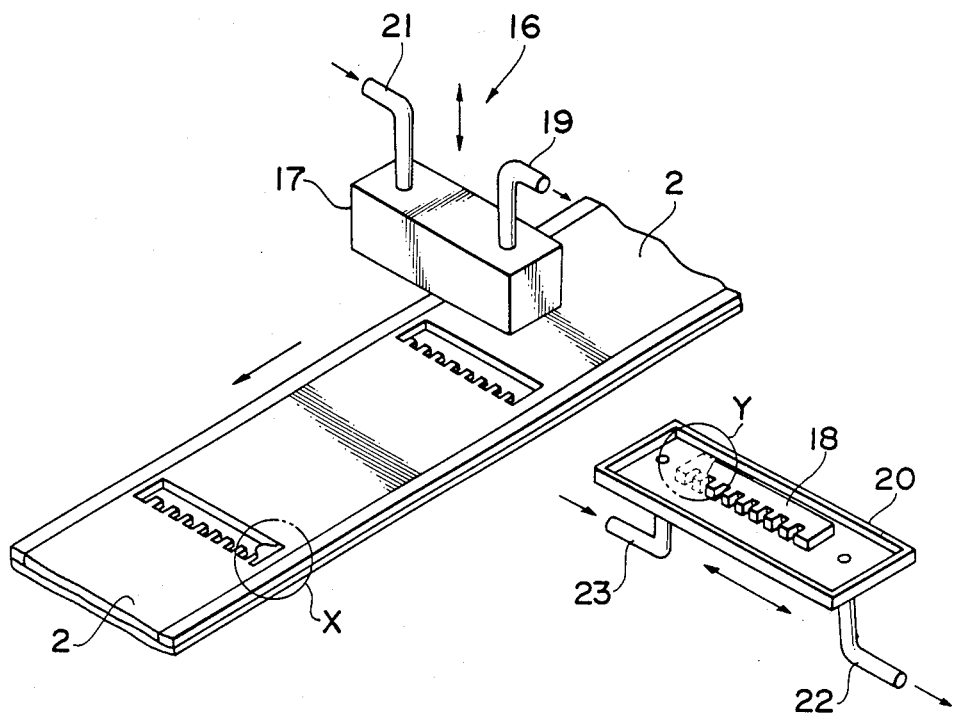
FIG. 6 is a perspective view of a conventional punching means including a removing means.

In FIG. 1, a pair of webs of the spacers are stuck on both sides of a web of the base film 3, and the gel membrane 2 is formed on the base film 3 by passing through the curing chamber 13 shown in FIG. 3. The half-assembled web moves intermitterntly in the leftward direction in FIG. 1. When the web is stopped, the puncher 24 descends, and punches the gel membrane 2 in an almost rectangular shape. Subsequently, the punched portion stops just under the adhering tape 26. At that time, the remover 25 is in the state of A of FIG. 2 where the adhering tape 26 is apart from the gel membrane 2 and the pressure roller 27 stops near the right end of the gel membrane 2 in the drawing. When the punched portion reaches just under the adhering tape 26, the pressure roller 27 descends and presses the adhering tape 26 to the surface of the cut piece of gel membrane 18 at an edge portion, as shown in FIG. 2B. The pressure roller 27 moves in the leftward direction in the drawing with pressing to the cut gel membrane piece 18. The cut piece of gel membrane 18 adheres to the adhering tape 26 by pressing, and is separated accompanying the adhering tape 26 from the base film 3 by the tension of the adhering tape, as shown in FIG. 2C. When the pressure roller 27 reaches the left edge of the cut piece 18 of gel membrane, as shown in FIG. 2D, the pressure roller 27 ascends as shown in FIG. 2E. The adhering tape 26 ascends together with the pressure roller 27, and the cut piece 18 of gel membrane is completely separated from the base film 3, as shown in FIG. 2F. Then, the pressure roller 27 returns to the original position, and a necessary length of the adhering tape 26 is wound to the take-up roll 29 so that a fresh part of the tape is located over the gel sheet, as shown in FIG. 2F. In this state, the remover wail till the next punched portion comes under the adhering tape 26. The web of gel sheet from which the cut piece 18 of gel membrane is removed is further conveyed intermittently, and the cover film 4 is attached and then cut by the cutter 15 to complete the gel sheet 1 for electrophoresis, as shown in FIG. 3.

When gel sheets were produced by the above process, not only the cut piece of gel membrane was surely and completely removed, but also the processing speed in raised to about four times compared to the prior art method.

The above process was also applied to the production of the gel sheet using a shark's teeth comb shown in FIG. 5, and a similar result was obtained.

I claim:

1. In a method of producing a gel sheet for electrophoresis comprising a gel membrane acting as the medium for electrophoresis composed of a hydrophilic polymer having a uniform thickness, two sheets of transparent or translucent electrical insulating films disposed on the front and the rear surfaces of the gel membrane and two spacers disposed along two facing sides of the gel membrane, wherein an end of the gel membrane is cut to form a slot for laoding samples, the improvement which comprises cutting out a portion of the gel membrane before one surface of the gel membrane is covered with said electrical insulating film in the shape of the slot for loading samples, pressing an adhering member on the cut-out portion of the gel membrane to adhere the cut-out, and removing the adhering member and attached cut-out portion from the gel membrane.

2. The method of claim 1 wherein plural wells for placing the samples are formed at the bottom of the slot.

3. The method of claim 1 wherein the bottom of the slot is substantially straight, and is divided into wells by using a plate member having a sawtooth-shaped portion of which respective projections are V-shaped.

4. The method of claim 1 wherein said adhering member is a tape having a hydrophilic surface.

5. The method of claim 1 wherein said adhering member is a paper tape having a hydrophilic surface.

* * * * *